(12) United States Patent
Young et al.

(10) Patent No.: US 7,385,684 B2
(45) Date of Patent: Jun. 10, 2008

(54) ANGULAR POSITION SENSOR

(75) Inventors: C. Gilbert Young, Winter Park, FL (US); Victor Tisdel, Winter Springs, FL (US)

(73) Assignee: Lockheed Martin Corporation, Orlando, FL (US)

( * ) Notice: Subject to any disclaimer, the term of this patent is extended or adjusted under 35 U.S.C. 154(b) by 249 days.

(21) Appl. No.: 10/945,836

(22) Filed: Sep. 21, 2004

(65) Prior Publication Data

US 2006/0064041 A1  Mar. 23, 2006

(51) Int. Cl.
G01C 11/26  (2006.01)
(52) U.S. Cl. .................. 356/139.05; 356/139.04; 356/139.07; 356/141.1; 356/152.3
(58) Field of Classification Search ...... 356/4.01–5.15, 356/152.1–152, 139.04, 139.05, 139.07, 356/141.1, 146
See application file for complete search history.

(56) References Cited

U.S. PATENT DOCUMENTS

| | | | | |
|---|---|---|---|---|
| 4,681,433 | A | * | 7/1987 | Aeschlimann ............... 356/5.1 |
| 5,187,540 | A | * | 2/1993 | Morrison ............... 356/139.03 |
| 5,771,978 | A | * | 6/1998 | Davidson et al. ........... 172/4.5 |
| 6,106,298 | A | | 8/2000 | Pollak ......................... 434/29 |
| 6,319,008 | B1 | | 11/2001 | Mickelson et al. ........... 434/29 |
| 6,320,284 | B1 | * | 11/2001 | Fontana et al. ............... 310/12 |
| 6,384,908 | B1 | * | 5/2002 | Schmidt et al. .......... 356/152.3 |
| 6,681,629 | B2 | | 1/2004 | Foxlin et al. .................. 73/488 |
| 6,753,828 | B2 | | 6/2004 | Tuceryan et al. .............. 345/8 |
| 2001/0035845 | A1 | * | 11/2001 | Zwern .......................... 345/8 |
| 2003/0011359 | A1 | | 1/2003 | Ashe ..................... 324/207.17 |
| 2003/0152290 | A1 | | 8/2003 | Odell ......................... 382/291 |
| 2003/0173953 | A1 | | 9/2003 | Ashe ..................... 324/207.17 |
| 2003/0233042 | A1 | | 12/2003 | Ashe ......................... 600/422 |
| 2004/0088136 | A1 | | 5/2004 | Ashe ......................... 702/150 |
| 2004/0135069 | A1 | | 7/2004 | Odell ...................... 250/208.2 |

OTHER PUBLICATIONS

Applied Science Laboratories, Technology and Systems for Eye Tracking, "Eyehead Integration", 4 pgs, Copyright 1998.
Applied Science Laboratories, Technology and Systems for Eye Tracking, Specifications, 2 pgs., Copyright 1998.
Applied Science Laboratories, Technology and Systems for Eye Tracking, Model H-HS-BN6 Binocular, 2 pgs., Copyright 1998.
Applied Science Laboratories, Technology and Systems for Eye Tracking, H-MOB6 Mobile Eyetracker, 2 pgs., Copyright 1998.
Applied Science Laboratories, Technology and Systems for Eye Tracking, High Speed Chinrest, 3 pgs., Copyright 1998.
Applied Science Laboratories, Technology and Systems for Eye Tracking, H HS6 High Speed, 2 pgs., Copyright 1998.
Applied Science Laboratories, Technology and Systems for Eye Tracking, Model H6, 3 pgs., Copyright 1998.

(Continued)

*Primary Examiner*—Thomas H. Tarcza
*Assistant Examiner*—Timothy A Brainard
(74) *Attorney, Agent, or Firm*—Welsh & Katz, Ltd.

(57) ABSTRACT

A head tracking system combines a plurality of sources of radiant energy, a plurality of sensors and at least one reflective element. As the reflective element moves, various radiant energy beams become incident thereon. The incident beams are reflected to respective sensors thereby providing head position signals.

15 Claims, 2 Drawing Sheets

OTHER PUBLICATIONS

Ascension Technology Corporation. Flock of Birds—Real-time Motion Tracking, Specifications, 2 pgs, Copyright 2000.

News Release—General Reality Company VR Performance Peripherals "General Reality Company Introduces Lowest-Cost Head Tracker in Virtual Reality Industry", 1 pg, Aug. 1, 1996.

J. Reimoto, Abstract, "A Vision-Based Head Tracker for Fish Tank Virtual Reality-VR Without Head Gear", Virtual Reality Annual International Symposium, Mar. 11-15, 1995, Research Triangle Park, NC, 1 pg.

* cited by examiner

ANGULAR POSITION SENSOR

FIELD OF THE INVENTION

The invention pertains to head trackers. More particularly, the invention pertains to optical head trackers which are relatively inexpensive and have relatively minimal set-up time.

BACKGROUND OF THE INVENTION

It has been known to use head trackers in simulators which are used in various types of equipment, such as flight simulators, vehicular simulators such as armored units or other types of land vehicles as well as water born vehicles. Many of the known types of head trackers provide multiple degrees of information, such as six degree of freedom in position and orientation information so that appropriate views or displays can be activated only as needed. Known multiple degree of head trackers have been based on various different technologies. These have included ultrasound, optical, inertial, or magnetic.

While known head trackers are effective for their intended purpose, they are often expensive and require extensive set-up times. Additionally, known head trackers often require substantial software interaction to address the various signals coming therefrom. This can include dedicating resources to carry out extensive plotting.

Certain types of simulations require information for only a single degree of freedom, for example, in the azimuthal direction. For example, armoured simulators, such as armored wheeled or tracked vehicles present to the vehicle commander a plurality of spaced-apart displays simulating cupola or tank turret periscopes which face different directions. In these instances, the vehicle commander would only need to rotate his or her head about a substantially fixed vertical axis to view displays presented at several different angles. Viewing directions could include, for example, straight ahead, 20 to 22 degrees to the right, 45 degrees to the right, and similar angles to the left.

Thus, there continues to be a need for head trackers which provide more limited amounts of information, corresponding to fewer degrees of freedom, than heretofore known. Preferably, such head trackers could be implemented more cost effectively than multiple degree of freedom head trackers of known types. Additionally, it would be preferable if set-up times could be reduced so that the speed of training or conducting exercises can be increased.

DETAILED DESCRIPTION OF THE EMBODIMENTS

Figure 1:
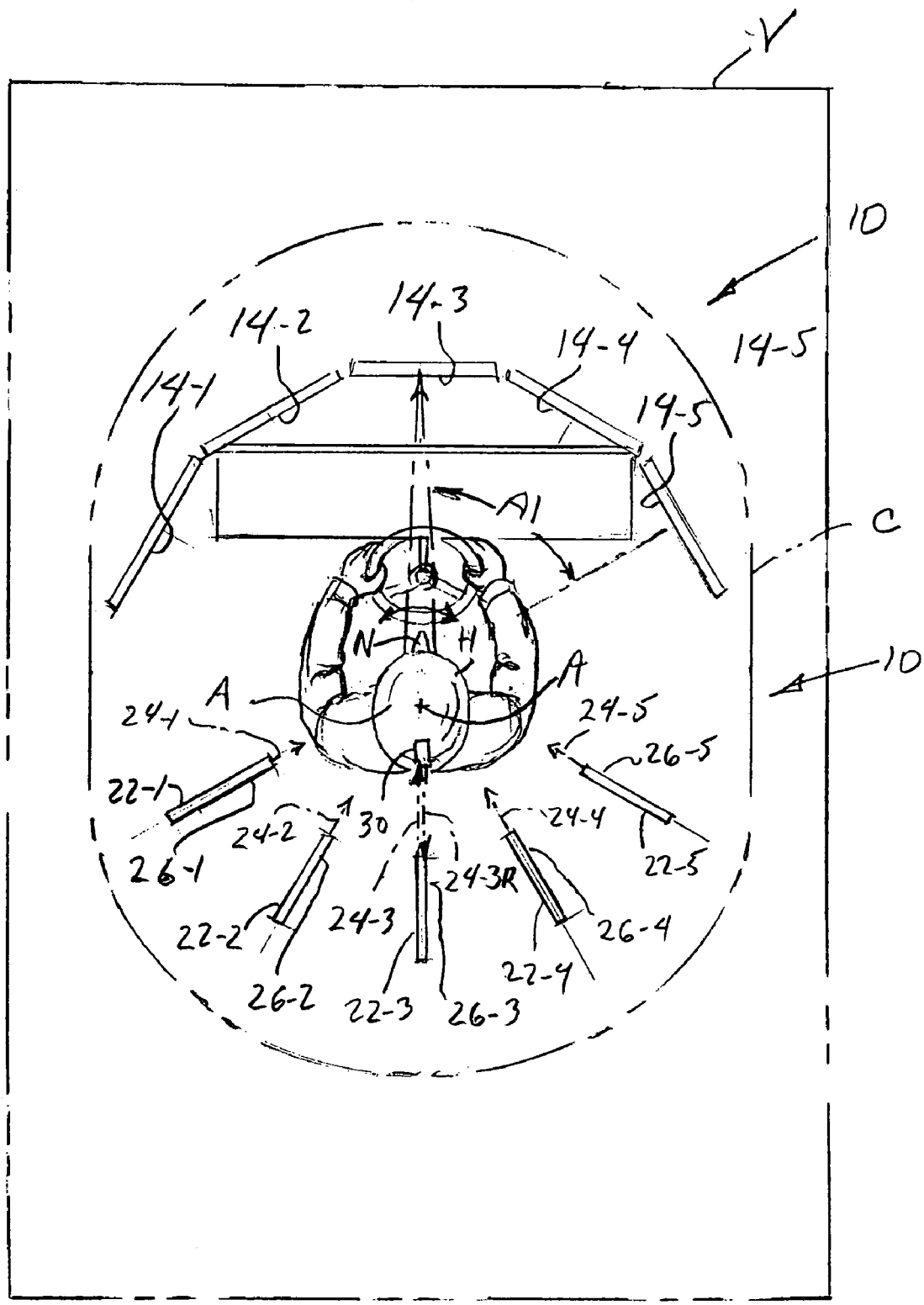
FIG. 1 is a top plan view of an apparatus in accordance with the present invention.

While embodiments of this invention can take many different forms, specific embodiments thereof are shown in the drawings and will be described herein in detail with the understanding that the present disclosure is to be considered as an exemplification of the principles of the invention and is not intended to limit the invention to the specific embodiment illustrated.

This invention provides a simple, low-cost means for determining a single-plane angular orientation of an object, such as a person's helmet in a simulator. This is accomplished in a disclosed embodiment by the use of fixed infra-red (IR) light sources spaced circumferentially around the helmet, pointing at the helmet. Reflective material placed at one point on the helmet. A detector is located near each light source to detect the reflected infra-red beam.

Some of the advantages of this embodiment of this invention are that they do not require complex equipment configurations. They are very low cost. Data processing does not require detailed plotting as many trackers do. They do not cause electromagnetic interference in displays and electronics as magnetic trackers sometimes do. Conventional head trackers cost several thousand dollars for the hardware. Embodiments of this invention can be implemented for no more than a few hundred dollars. Set-up time for conventional head trackers can be several man months. For embodiments of this invention it is a matter of a few man days.

One embodiment of this invention uses several similar infra-red (IR) sources angularly displaced around the helmet position and directed toward the geometric center of the cupola, where the helmet is normally centered. The helmet has a retroreflective material, which could be a retro-reflective tape, attached to it so that each IR source illuminates the retro-reflector, in turn, as the head is rotated about a vertical axis.

IR detectors, each placed close to a respective IR source, detect the retro-reflected light only from the respective IR source, and only when the retro-reflective material is within the IR beam. In this way the angular position of the helmet is determined, well enough to determine which of the several discrete displays is being viewed by an operator. In this way display generating capacity can be conserved by only providing imagery to those displays viewable by the operator or trainee.

Figure 2:
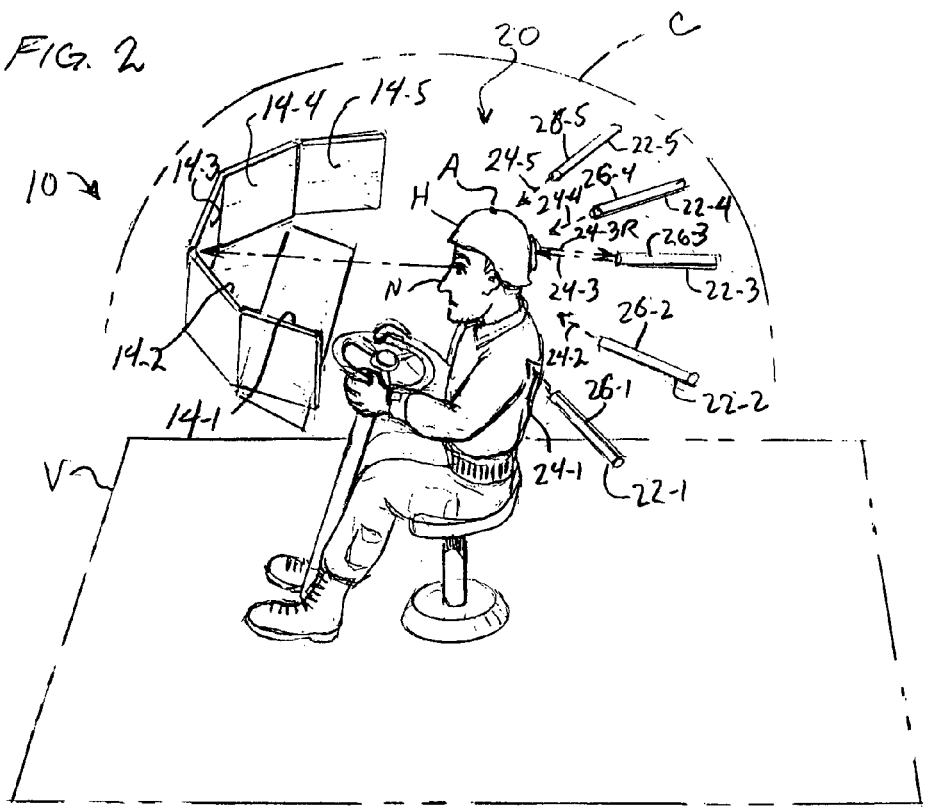
FIG. 2 is a side elevational view of the apparatus of FIG. 1.

FIGS. 1 and 2 are a top plan view and a side elevational view, respectively, of an exemplary vehicular simulator, such as a simulator for an armored vehicle which might have a turret or a cupola. Periphery views in the turret or cupola are in part simulated by a plurality of displays or display units 14-1, -2, -3, -4, -5. The displays 14-1 . . . -5 are dispersed around an axis of rotation A.

The axis of rotation A corresponds to an axis of rotation about which a human operator H with a nose N rotates his/her head from a straight ahead rotation to the right or left, depending on the requirements of the training exercise or the simulation. A display generator, best seen in FIG. 3, energizes some, but not necessarily all, of the displays 14-1 . . . -*n* depending on the position of the nose N of the operator H.

A head positioning system in accordance with the invention is in part indicated generally at 20 and can be incorporated into the simulator 10 as described subsequently. The system 20 incorporates a plurality of sources 22-1, 22-2 . . . 22-5 of beams of radiant energy, of a selected frequency, such as infra-red or visible red. The sources, such as 22-1 transmit a respective beam of radiant energy 24-1 . . . 24-5 toward the axis A. The operator or trainee H might be wearing a helmet which carries a reflective material indicated generally at 30 thereon. The material 30 is selected such that it will reflect radiant energy at the frequency of the respective source or sources 22-1 . . . -*n*.

A respective sensor, 26-1 . . . -5 is associated with each of the sources 22-$i$. Each of the sensors 26-$i$ is responsive to incoming or sensed radiant energy, such as radiant energy 24-3R which has been reflected off of surface 30 and as result, is incident on sensor 26-3.

As the trainee or operator H rotates his/her head about the axis A, the reflective surface 30 is arcuately moved about the axis A and can reflect a different beam of incident radiant energy, for example, beam 24-1 which would then be reflected back to sensor 26-1 in the event that the nose N of the trainee or operator has been rotated so as to be directed toward the display 14-5. The source/sensor combinations 22-1, 26-1 provide signals to a related control system, which could include a programmable processor, best seen in FIG. 3, indicative of an azimuthal parameter indicated in phantom on FIG. 1 by angle A1.

It will be understood that neither the exact number or type of sources of radiant energy or sensors are limitations of the present invention. The number to be used would be determined by the type of simulator as would be understood by those of skill in the art. Similarly, the frequency of the transmitted beams of radiant energy is not a limitation of the present invention.

The exact configuration of a source/sensor combination is not a limitation of the present invention. Sources and respective sensors can be carried in a common housing. Alternately, separate housings can be used. The configuration of source and sensor can be coaxial if desired. Other combinations and orientations are possible and all come within the spirit and scope of the present invention.

Figure 3:
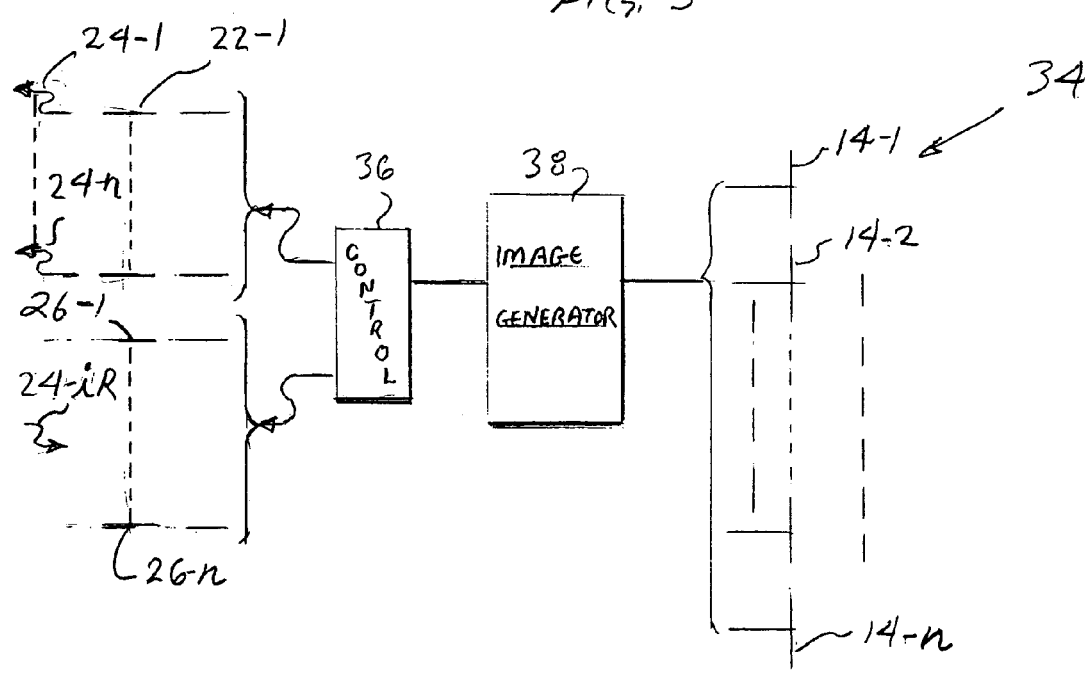
FIG. 3 is a block diagram of a system in accordance with the invention.

FIG. 3 illustrates system 34 in accordance with the invention. The plurality of sources 22-1 . . . -$n$ is driven from control circuitry, which could include a programmed processor, 36. The control circuitry 36 provides overall control functionality to carry out the desired simulation or training exercise.

Sensors 26-1 . . . -$n$ are coupled to control circuitry 36. The sources 22-1 generate respective beams of radiant energy 24-1. As indicated above, the beams of radiant energy can be of various frequencies, infra-red or visible. Alternately, it should be understood that the sources 22-1 . . . -$n$ need not emit the same frequencies. The sources 22-1 . . . -$n$ could in fact emit different respective frequencies, as would be understood by those of skill in the art.

The sensors 26-1 . . . -$n$ respond to received incident energy of the appropriate frequency, such as respective incident energy 24-$i$R. In accordance with the embodiment of FIGS. 1 and 2, only one of the sensors will receive reflected signal depending on the position of reflective element 30. It will be understood that other embodiments of the invention are possible. These include a plurality of reflective elements spaced around the helmet of the trainee or operator H. The plurality of reflective elements would generate a plurality of reflected beams, similar to 24-$i$R, but a multiplicity thereof, directed toward respective sensors such as sensors 26-1, -2, . . . -$n$. In such instances, the control computer 36 will received a plurality of signals from the sensors 26-1 . . . -$n$ indicative of position of the head of the operator H. All such variations come within the spirit and scope of the present invention.

Control circuitry 36 also provides feedback azimuthal signals to image generator 38. Generator 38 in turn drives respective members of the plurality displays 14-1 . . . 14-$n$ with signals to present an appropriate image on those display units which are individual fields of vision of the trainee or operator H. For example, if the operator or trainee H is looking straight ahead, as in FIG. 1, displays 14-2, -3 and -4 could be activated with the appropriate display as those would be within the expected field of vision of the operator or trainee H. Displays 14-1, -5 could be displaying an image if desired but the image would not necessarily be the current imagery as seen in displays 14-2, -3 and -4. With other orientations of the nose N of the trainee or operator H, other combinations of display units could be energized with the current appropriate display segment From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. A tracking system comprising:
   a plurality of source, sensor combinations, for each combination, the source and the sensor are located adjacent to one another situated on a line relative to a common axis, the combinations being circumferentially situated relative to each another about the axis;
   each source projecting a beam of electromagnetic energy, each sensor responding to a reflection of the beam;
   a beam reflector rotatably located relative to the axis at a predetermined distance from the plurality of source, sensor combinations to reflect the beam to each sensor only when the reflector is located on the line between the axis and the respective combination.

2. A system as in claim 1 where the reflector is rotatable about the common axis and the combinations define an arc located at substantially the predetermined distance from the common axis.

3. A system as in claim 2 where the arc extends in a plane perpendicular to the common axis.

4. A system as in claim 2 where the beam extends along a central axis with the common axis and the central axis defining a plane.

5. A system as in claim 2 where the arc is rotatable to define at least one circle.

6. A system as in claim 5 which includes control circuitry coupled to at least the combinations, the control circuitry establishing a location of the reflector.

7. A system as in claim 6 where the established location comprises an azimuthal parameter.

8. A system as in claim 1 where the source and the sensor combinations are each carried by a respective common housing.

9. A system as in claim 1 where the members of the plurality of source/sensor combinations are uniformly dispersed about the common axis with the reflector rotatable about the axis equidistant from the combinations.

10. A system as in claim 9 which includes at least a second beam reflector, displaced from the at least one reflector.

11. A system as in claim 10 where the reflectors rotate about the common axis and, responsive thereto, respective sensors emit location specifying signals.

12. A system as in claim 11 which includes software responsive to the location specifying signals to activate respective displays.

13. A system as in claim 12 where the location specifying signals define a viewing orientation, relative to the axis thereby establishing which members of a plurality of displays should be activated.

14. A display as in claim 13 where the software alters the active members in response to an altered viewing orientation.

15. A system as in claim 1 where the reflector comprises a piece of reflective tape.

* * * * *